United States Patent [19]
Tanikawa et al.

[11] Patent Number: 4,461,558
[45] Date of Patent: Jul. 24, 1984

[54] ENDOSCOPIC PHOTOGRAPHING APPARATUS

[75] Inventors: Kowji Tanikawa; Koichi Matsui, both of Tokyo; Tetsuya Kimura, Fujiyoshida; Takeshi Takamatsu, deceased, late of Hachioji, all of Japan; by Tokuyuki Takamatsu, legal representative, Tokyo, Japan

[73] Assignee: Olympus Optical Co., Ltd., Tokyo, Japan

[21] Appl. No.: 407,881

[22] Filed: Aug. 13, 1982

[30] Foreign Application Priority Data

Aug. 17, 1981 [JP] Japan ................. 56-128444

[51] Int. Cl.³ ................. A61B 1/04; A61B 1/06
[52] U.S. Cl. ................. 354/416; 354/459; 354/475; 354/62; 328/6
[58] Field of Search ............. 354/50, 60 R, 62, 60 F, 354/126, 145, 416, 417, 459, 475, 145.1; 128/6-9

[56] References Cited
U.S. PATENT DOCUMENTS
4,343,300 8/1982 Hattori .................. 354/62 X Primary Examiner—William B. Perkey

[57] ABSTRACT

An endoscopic photographing apparatus comprises an endoscope, an endoscopic camera and a light supply unit. A CPU is incorporated into at least one of the endoscopic camera and light supply unit to discriminate the kind of the other. The CPU achieves its kind discrimination depending upon whether a response is present or not after a certain time period since the generation of a flag signal. Further, the CPU achieves its kind discrimination depending upon whether it receives the flag signal or not within a certain time period since the start of its operation.

7 Claims, 14 Drawing Figures

ENDOSCOPIC PHOTOGRAPHING APPARATUS

BACKGROUND OF THE INVENTION

The present invention relates to a photographing apparatus and, more particularly, a photographing apparatus for use to the endoscope.

The endoscopic photographing apparatus comprises an endoscope, an endoscopic camera and a light source unit, and these component means, that is, endoscope, endoscopic camera and light source unit are various in their kinds. There has been developed an endoscopic camera into which a CPU is incorporated so as to enable photographing to be achieved under computer control. When this newly-developed endoscopic camera is to be combined with a conventional light supply unit, however, a matching adaptor is needed, which is inconvenient to the user.

SUMMARY OF THE INVENTION

The object of the present invention is to provide an endoscopic photographing apparatus applicable to all kinds of endoscope component units.

According to the present invention, at least one of endoscopic camera and light supply unit is provided with means for discriminating the kind of the other in an endoscopic photographing apparatus comprising at least an endoscope, endoscopic camera and light supply unit.

DETAILED DESCRIPTION OF THE PREFERRED EMBODIMENTS

Figure 1:
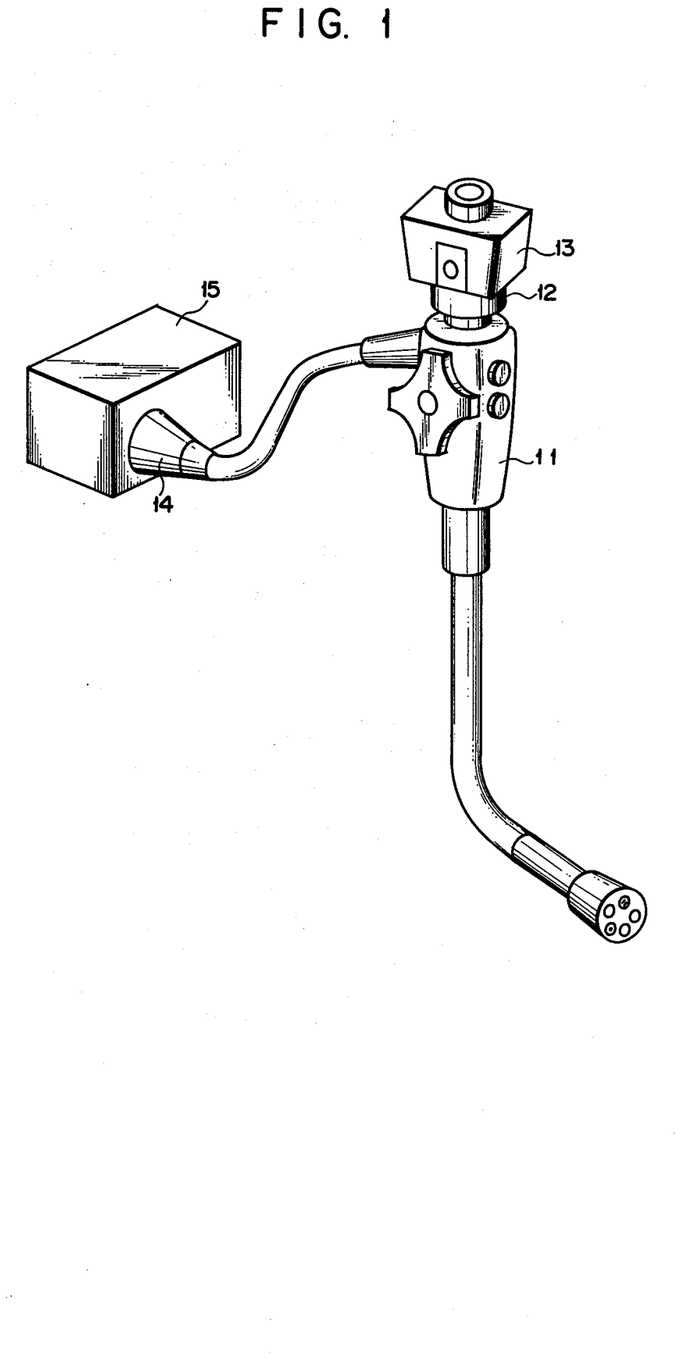
FIG. 1 is a perspective view showing an example of endoscopic photographing apparatus according to the present invention.

As shown in FIG. 1, an endoscopic photographing system comprises an endoscope 11, an endoscopic camera 13 attached to an eyepiece 12 of the endoscope 11, and a light supply unit 15 to which a connector 14 of the endoscope 11 is connected.

Figure 2:
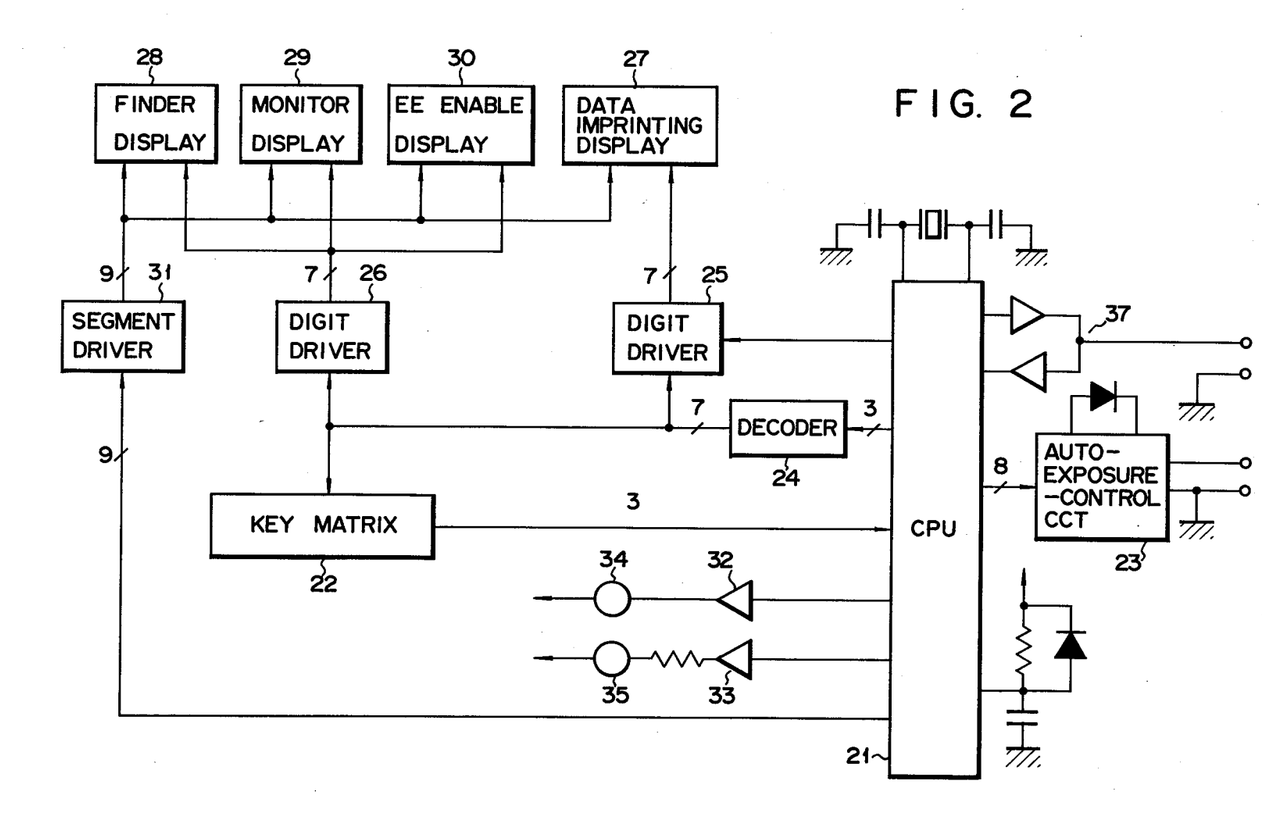
FIG. 2 is a circuit diagram showing the circuit section of an endoscopic camera.
Figure 3:
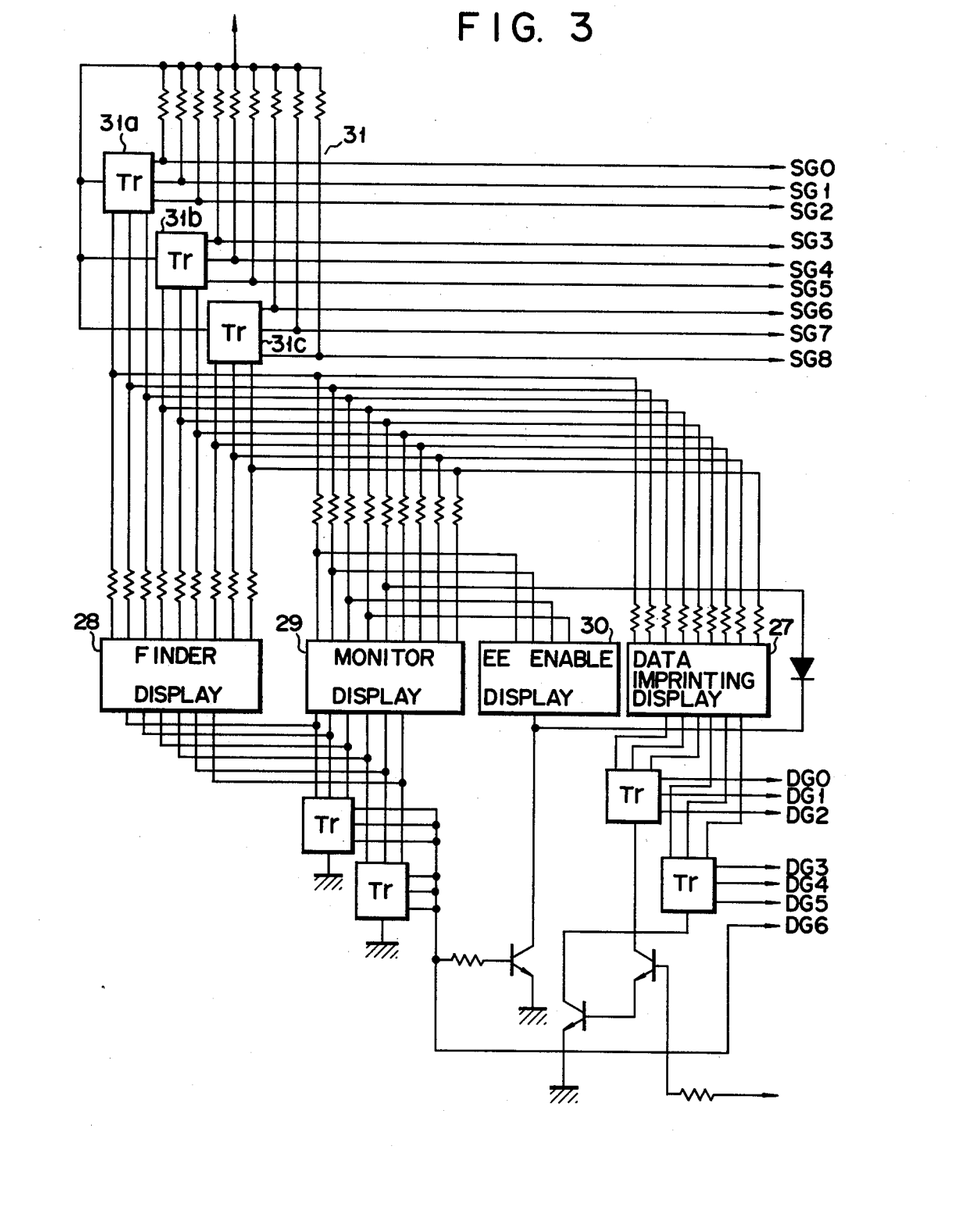
FIG. 3 is a circuit diagram showing in detail the display system of circuit section shown in FIG. 2.
Figure 4:
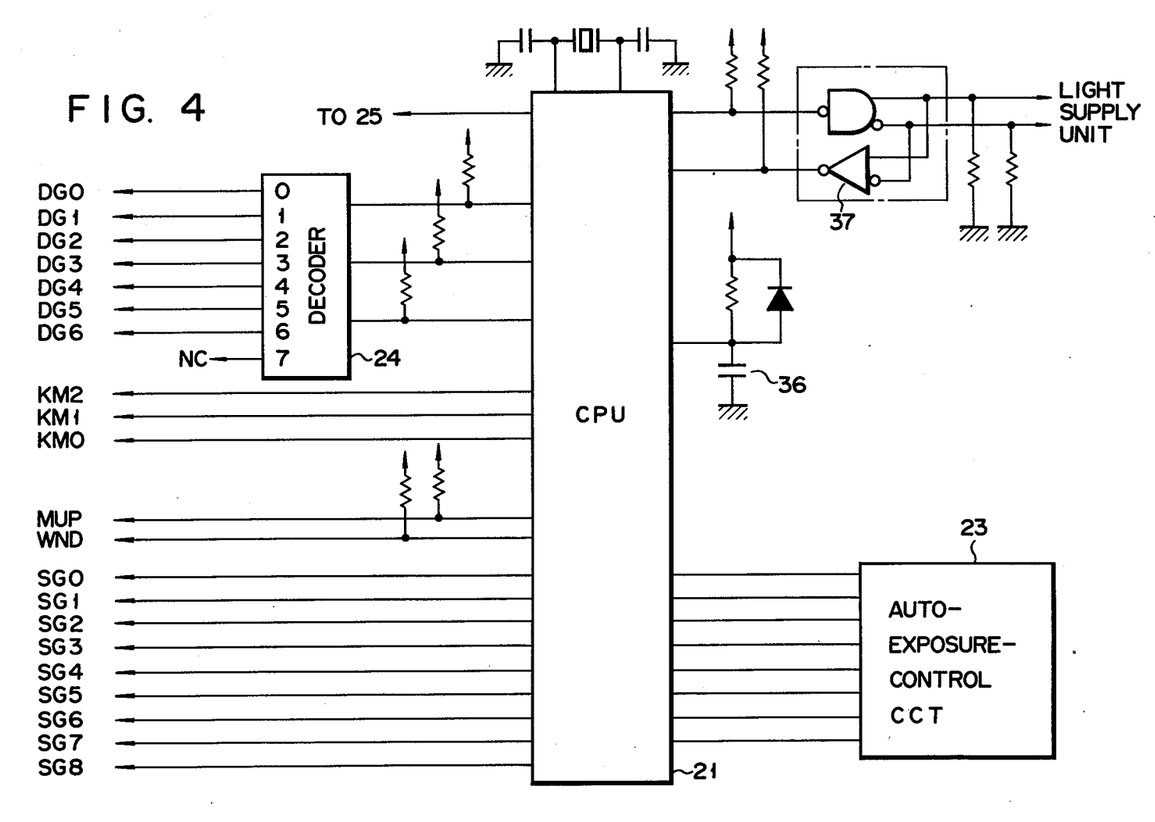
FIG. 4 is a circuit diagram showing the control system of endoscopic camera.

As shown in FIG. 2, the endoscopic camera 13 is provided with a CPU 21 to which a key matrix 22 and an auto-exposure control circuit 23 are connected and to which digit drivers 25 and 26 are also connected via a decoder 24. The digit driver 25 is connected to a data imprinting display 27 while the digit driver 26 to a finder display 28, a monitor display 29 and an EE enable display 30. Segment terminals of these displays 27 to 30 are connected to a segment driver 31. FIG. 3 shows these displays 27 to 30 and their periphery circuits. Signal lines SG0 to SG2, SG3 to SG5 and SG6 to SG8 are connected to segment driver transistor circuits 31a, 31b and 31c, respectively. Digit driver transistor circuits are connected to digit terminals of the displays 28 and 29 while digit driver transistor circuits connected to signal lines DG0 to DG5 are connected to the display 27. Signal lines DG0 to DG6 are connected to the 3-to-8 decoder 24, as shown in FIG. 4. The seventh terminal of this 3-to-8 decoder 24 is not connected. Because, a time of about 20 ms lapses from when power supply is turned on to when the CPU 21 is reset by a reset circuit 36, and the I/O port of CPU 21 outputs indefinite data during this time period so that segments of displays 27 to 30 are all turned on. The arrangement of leaving the seventh terminal of 3-to-8 decoder 24 open is intended to prevent the occurrence of this case. Namely, when all of input terminals of decoder 24 are "1", output is fed only through the seventh terminal because this seventh terminal is left floating, thus causing displays 27 to 30 to display nothing.

Figure 5:
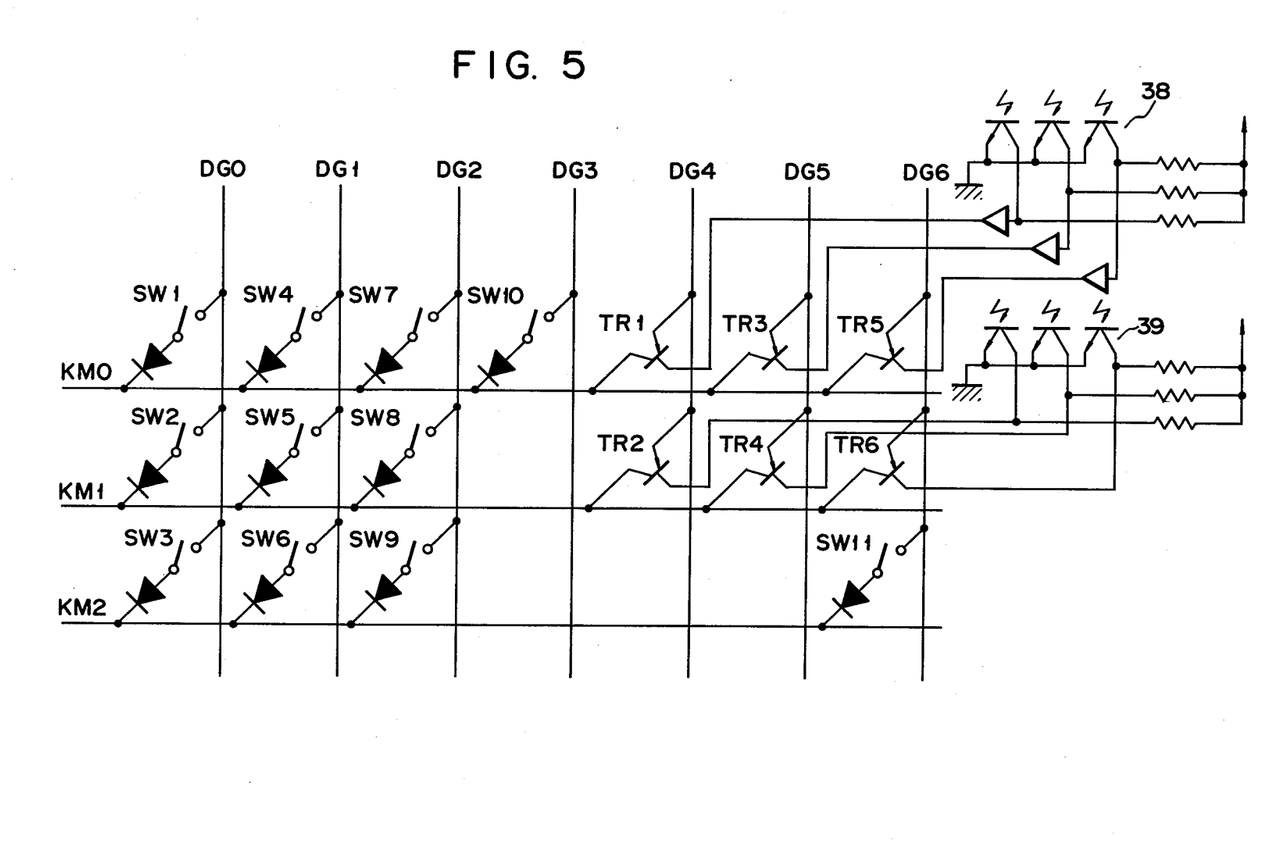
FIG. 5 is a circuit diagram showing a key matrix shown in FIG. 2.

The CPU 21 is connected to driver circuits 32 and 33 to control film winding and mirror-up motors 34 and 35. The CPU 21 is also connected through signal lines SG0 to SG8 to the segment driver 31. The CPU 21 is further connected through a dual transmission line 37 to the light supply unit 15. The key matrix 22 is arranged as shown in FIG. 5, matrices related to signal lines DG0 to DG3 have the function of setting imprinted data, switches SW1 to SW3 are camera back lid and camera ID discriminating switches, switches SW4 to SW6 are mode switches, and switches SW7 to SW10 are numeral and character selecting switches. A release switch SW11 is connected to the signal line DG6. Transistors TR1 to TR6 are controlled by phototransistor circuits 38 and 39 to respond to detections of mirror flip-up, start film-frame, film winding, end film-frame, film feeding of constant length and 20/40 exposure discrimination. When mirror flip-up is finished, for example, an LED (not shown) is turned on and its corresponding transistor 38 detects the light of LED to turn on the transistor TR1. The signal line DG4 is thus connected to a signal line KM0 to render the data imprinting display 27 operative. Imprinting data are set by the numeric key switch SW7 and character key switches SW8 to SW10.

Figure 6:
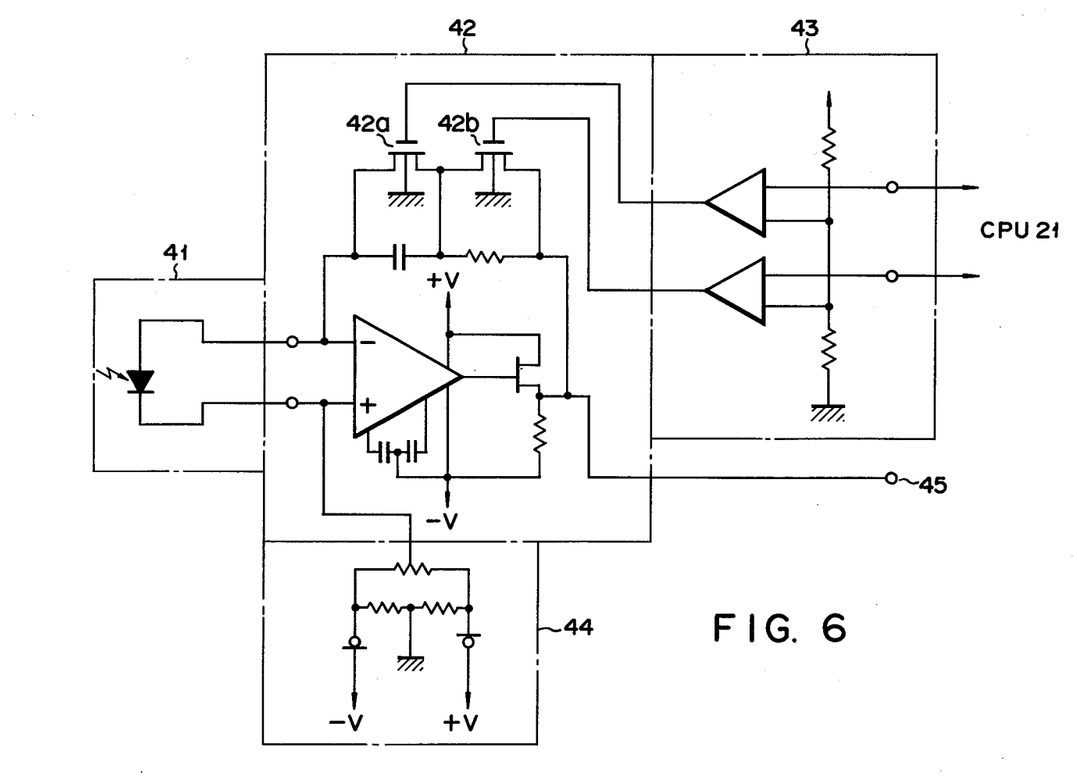
FIGS. 6 and 7 are circuit diagrams showing an automatic exposure calculating circuit section shown in FIG. 2.
Figure 7:
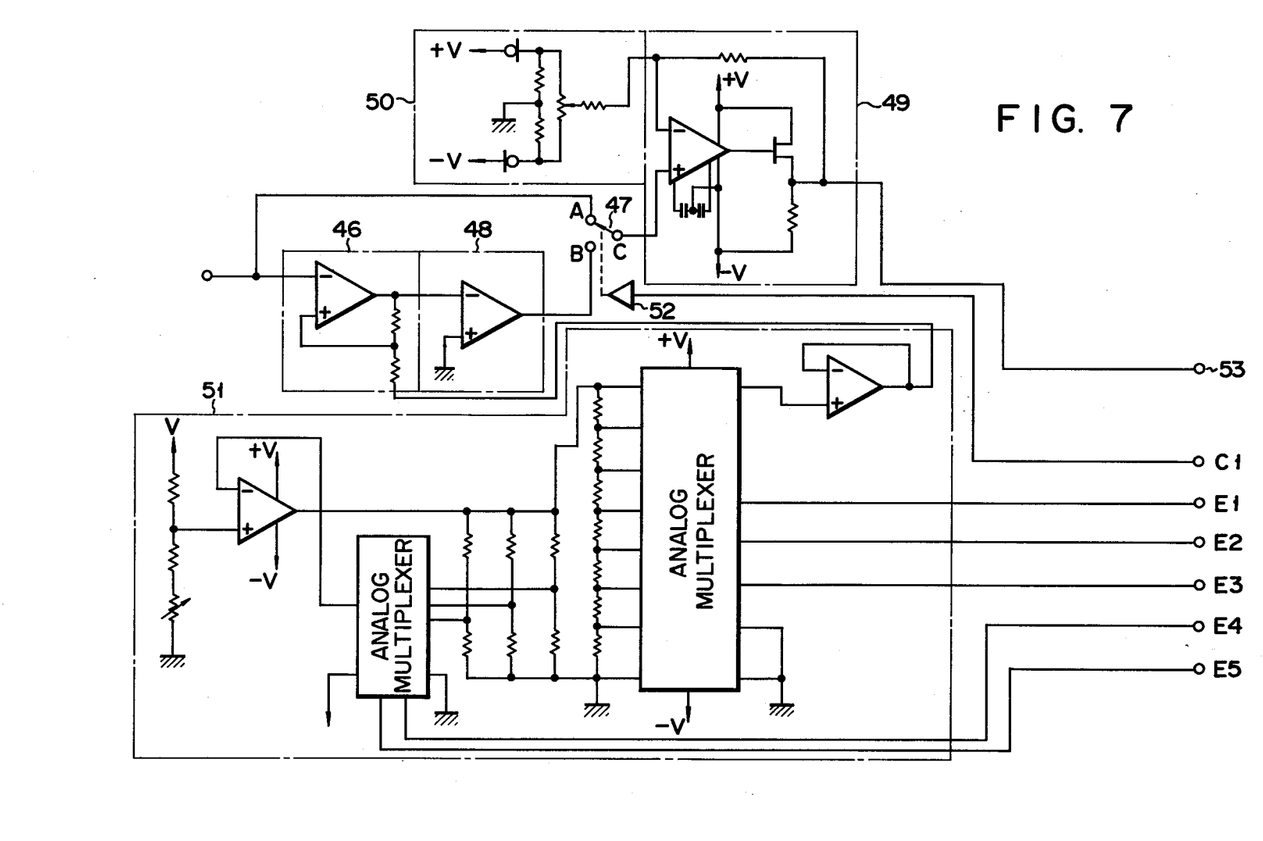

The auto-exposure control circuit 23 arranged as shown in FIGS. 6 and 7. A photosensor 41 is connected to an amplifier/integrator circuit 42, which is switched by an amplifier-to-integrator switching circuit 43 to achieve either of amplifying and integrating operations. An offset current of amplifier/integrator circuit 42 is eliminated by the output of a current offset adjustor 44. The output terminal 45 of the amplifier/integrator circuit 42 is connected to a comparator circuit 46 and a terminal A of a switch 47 shown in FIG. 7. An output of comparator circuit 46 is connected through an inverter circuit 48 to a terminal B of switch 47. A common terminal C of switch 47 is connected to an amplifier circuit 49. An offset voltage of this amplifier circuit 49 is eliminated by the output of a voltage offset adjustor 50. A reference voltage generator circuit 51 is connected to the reference voltage input terminal of a comparator circuit 46. The reference voltage generator circuit 51 generates a reference voltage corresponding to a selected one of to exposure constants applied to terminals E1 to E5 thereof. A switching signal is supplied through a terminal C to a switch driver 52 to switch the terminal from A to B and vice versa. The output of this autoexposure control circuit or amplifier circuit 49 is transmitted through an output terminal 53 to the light supply unit 15.

Figure 8:
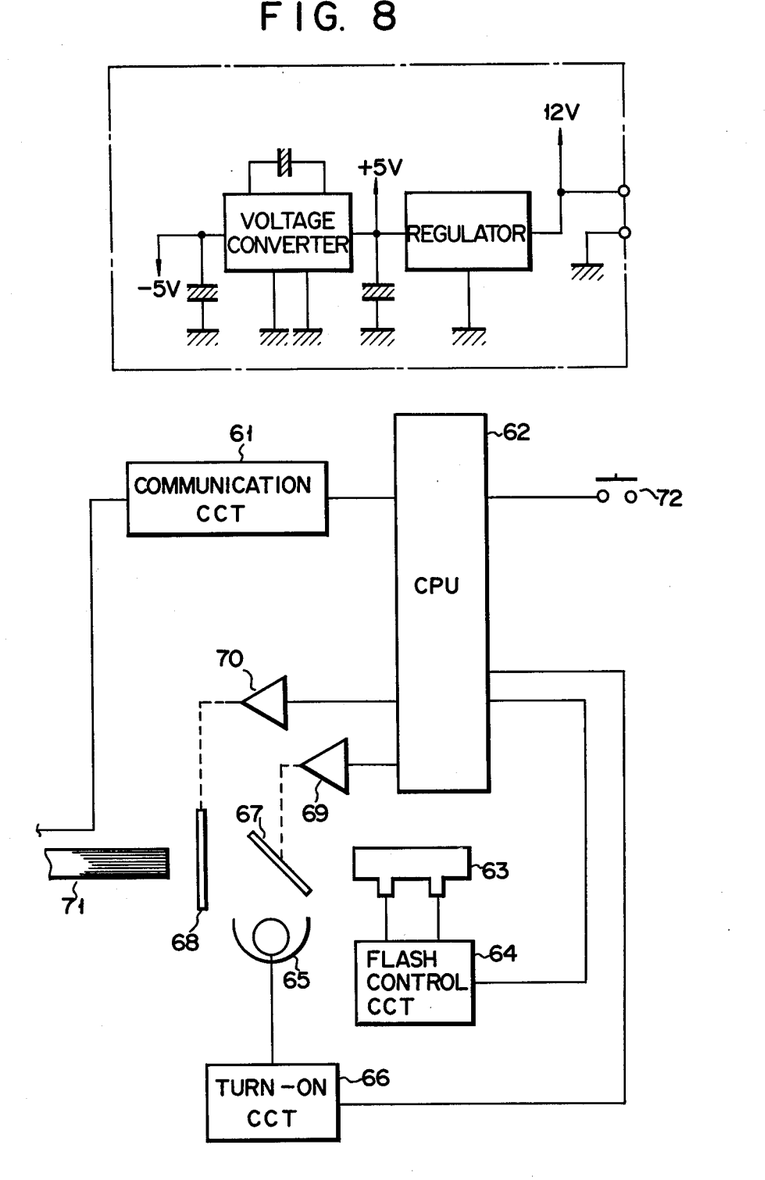
FIG. 8 is a circuit diagram showing a light supply unit.

When the light supply unit 15 is an improved one, it is provided with a bidirectional communication circuit 61 and a CPU 62 is connected through this communication circuit 61 to the transmission line 37 of endoscopic camera 13. The output terminals of CPU 62 are connected to a flash control circuit 64, which controls the flash of a strobo tube 63, and a turn-on circuit 66, which controls the turn-on of a lamp 65, while to mirror and shutter driver circuits 69 and 70, which drive a light path exchanging mirror 67 and a light source shutter 68, respectively.

Figure 9:
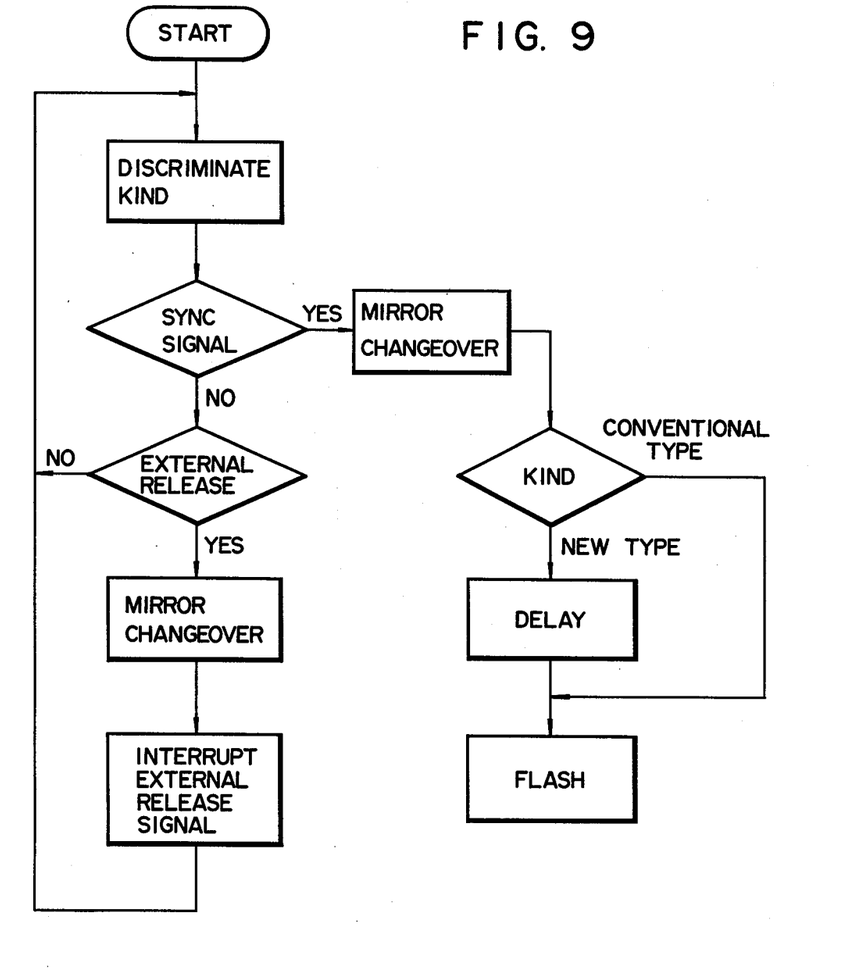
FIGS. 9 through 11 are flow charts showing the operation of endoscopic photographing apparatus according to the present invention.
Figure 10:
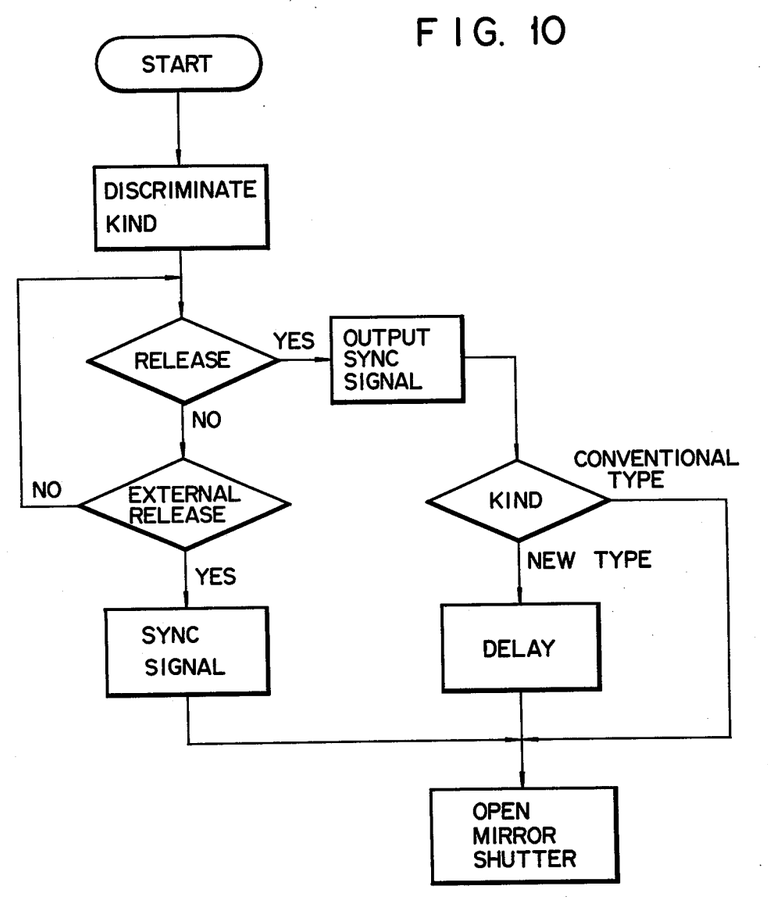
Figure 11:
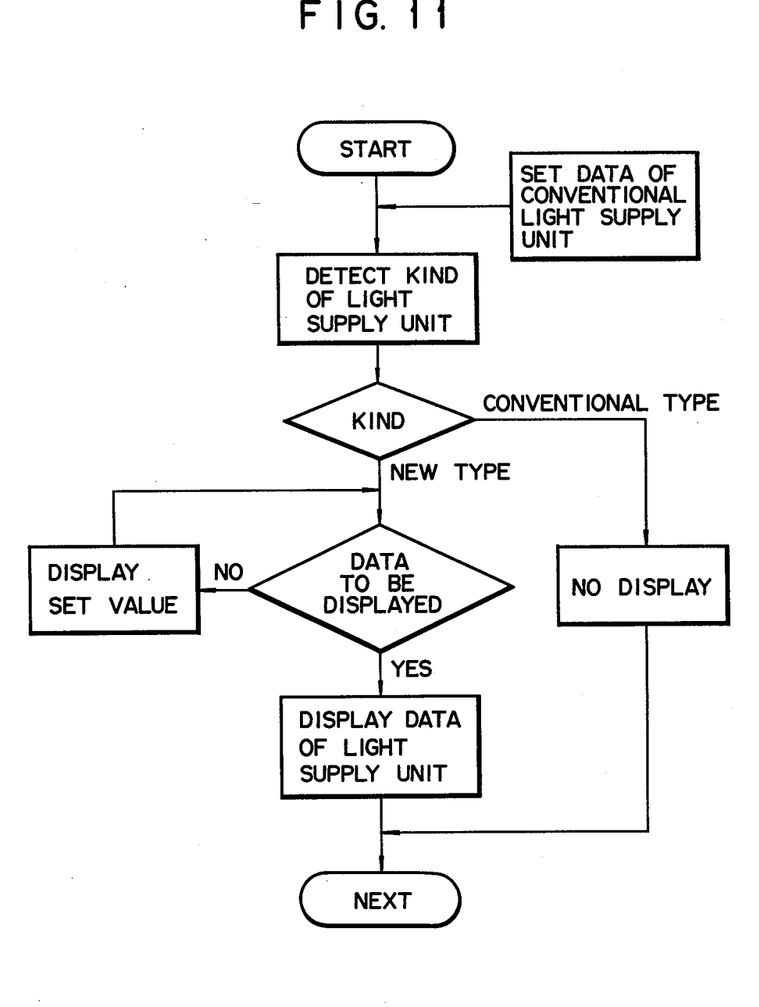

There will now be described the operation of endoscopic photographing apparatus having such arrangement as described above. When photographs are to be taken, the endoscopic camera 13 is attached to the eyepiece 12 of the endoscope 11 and the connector 14 of the endoscope 11 is connected to the light supply unit 15. When a power source 71 of the light supply unit 15 is turned on, the CPU 62 of light supply unit 15 feeds a flag signal to discriminate the model of endoscopic camera 13 connected. This flag signal is transmitted through the light supply unit communication circuit 61 to the transmission line 37 of the endoscopic camera 13 and received through this transmission line 37 by the CPU 21 of the endoscopic camera 13. This CPU 21 outputs a response signal in response to the flag signal. When this response signal is detected by the CPU 62 via the transmission line 37 and light supply unit communication circuit 61, the CPU 62 arranged on the side of light supply unit discriminates that the endoscopic camera 13 connected is of a new model. The CPU 21 of the endoscopic camera 13 discriminates, when it receives the flag signal, that the light supply unit 15 is of a new model. These states are shown by light supply unit and camera flow charts in FIGS. 9 and 10. Display signals of the CPU 21 of the endoscopic camera 13, that is, display signals to be applied to the 3-to-8 decoder 24 shown in FIG. 4 are all kept level "1" during the model discrimination or search process and output of decoder 24 is thus allowed to apply only through its seventh terminal. Therefore, none of displays 27 to 30 performs displaying operation. These displays 27 to 30 perform their displaying operations when EE enable display signal is generated, and a time of from 0.7 to 1 second is needed from the turn-on of power source to the generation of EE enable display signal. This EE enable display is shown by the flow chart in FIG. 11. According to this flow chart, it is checked by the CPU 21 of the endoscopic camera 13 whether or not display data is fed from the light supply unit 15 when the flag signal of light supply unit 15 has been detected and the light supply unit 15 has been found to be of new model. When no display data is present, the data set in the endoscopic camera 13 is displayed and the data input from the light supply unit 15 is again checked.

Figure 12:
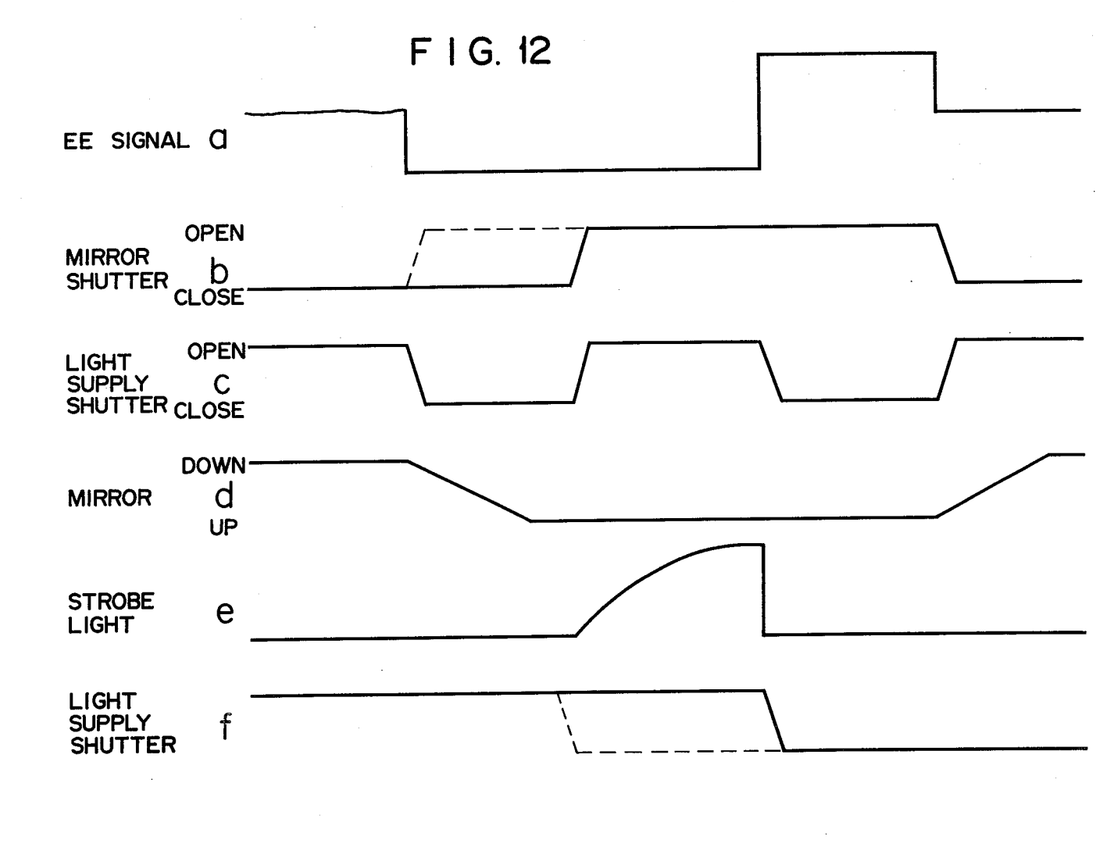
FIGS. 12 through 14 are time charts showing the operation of endoscopic photographing apparatus according to the present invention.

As shown in FIG. 12, the light source shutter 68 (FIG. 8) of light supply unit 15 is opened under this state and the light of the lamp 65 is turned by the light path exchanging mirror 67 to come incident upon the endoscope light guide 71, illuminating an object through the endoscope 11, and light reflected comes incident upon the endoscopic camera 13 through an image guide (not shown) to render the photosensor circuit 41 of auto-exposure control circuit section 23 operative. A signal appearing through the EE line or signal a appearing at the output terminal 53 (FIG. 7) is shown in FIG. 12. When the release button 16 of the endoscopic camera 13 is then pushed, the release switch SW11 (FIG. 5) is closed to generate a sync signal. In response to the sync signal, the light path exchanging mirror 67 in the light supply unit 15 starts its light path exchanging operation as shown by (d) in FIG. 12 while the light source shutter 68 is closed as shown by (c) in FIG. 12. The opening of a mirror shutter (not shown) of the endoscopic camera 13 is delayed this time and when the light path exchanging mirror 67 finishes its light path exchanging operation completely, mirror and light source shutters of camera are opened as shown by (b) and (c) in FIG. 12. The strobo tube 63 of the light supply unit 15 emits light this time as shown by (e) in FIG. 12. The auto-exposure control circuit 23 starts its EE calculation, synchronizing with the generation of sync signal. Namely, when integration command is applied from the CPU 21 to the amplifier/integrator switching circuit 43 in FIG. 6, synchronizing with the sync signal, the amplifier/integrator switching circuit 43 turns OFF a switching element 42a but ON a switching element 42b. The circuit 42 is thus caused to operate as an integrator, integrating photosignal of photosensor 41. The integration output of circuit 42 is supplied through the terminal 45 to the comparator 46 in FIG. 7 and compared with reference voltage of reference voltage generator 51. The reference voltage generator 51 outputs the reference voltage corresponding to the exposure constant applied from the CPU 21 via terminals E1 to E5. When the integration output reaches the reference voltage or when right exposure is obtained, the comparator 46 generates an output signal. This output signal is inverted by the inverter 48 and applied through the switch 47 to the amplifier 49. The switch 47 is turned to the contact B by a switching signal applied from the CPU 21, synchronizing with the sync signal. An EE signal is applied from the amplifier 49 and transmitted through the terminal 53 to the flash control circuit 64 of the light supply unit 15. In response to the EE signal, the flash control circuit 64 terminates the flash radiation of the strobo tube 63 and the light supply shutter 68 is closed as shown by (e) and (c) in FIG. 12. The mirror shutter of camera is closed by the signal a of the EE circuit 23, as shown by (b) in FIG. 12, and the light path exchanging mirror 67 is returned to its original position, as shown by (d) in FIG. 12.

Although the opening of the mirror shutter of the camera is delayed from the generation of sync signal to the changeover finish of light path exchanging mirror in the above-described operation, the mirror shutter is opened synchronizing with the generation of sync signal, as shown by a broken line (b) in FIG. 12, when the light supply unit 15 is not of new model or when the conventional model of the light supply unit is employed. Therefore, the photograph taken is fogged due to the light of the lamp 65. Opening and closing operations of the conventional model of light source shutter 68 are shown by (f) in FIG. 12.

Figure 13:
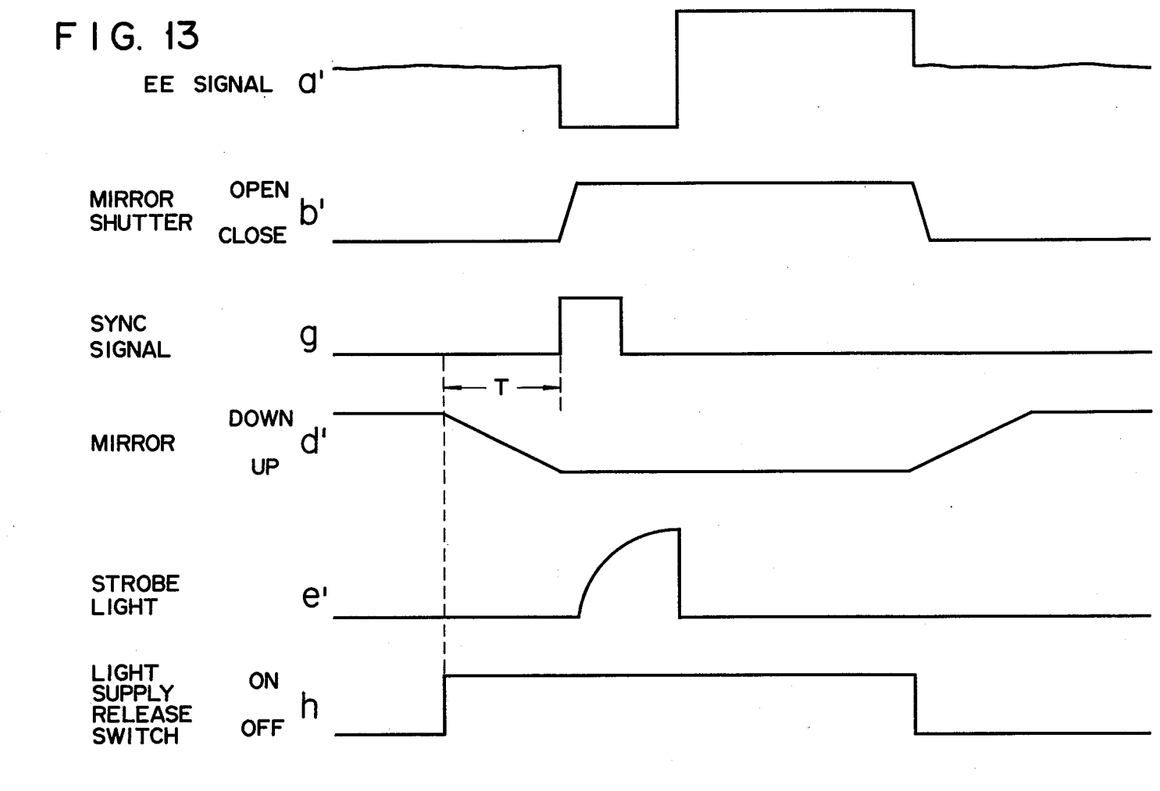

Although release is effected in the endoscopic camera 13 in the above, a case where release is achieved in the light supply unit 15 will be described referring to the time chart shown in FIG. 13. When the light source release switch 72 is closed as shown by (h) in FIG. 13, a sync signal g is applied to the endoscopic camera 13 after the transmission delay of time T. The light path exchanging mirror 67 starts its light path exchanging operation this time. Synchronizing with the sync signal g transmitted, the mirror shutter is opened in the endoscopic camera 13 as shown by (b') and EE calculation is started. When the mirror shutter is completely opened, the strobo tube 63 of the light supply unit 15 is flashed. When optimum amount of exposing light is obtained and an EE output is generated, the flashing of strobo tube 63 is stopped as shown by (e').

When release is effected in the light supply unit 15 as described above, the mirror shutter is opened synchronizing with the sync signal applied after the transmission delay. When the light path exchanging time of light path exchanging mirror is longer than the transmission delay time, fogging is caused due to light of the lamp 65.

Figure 14:
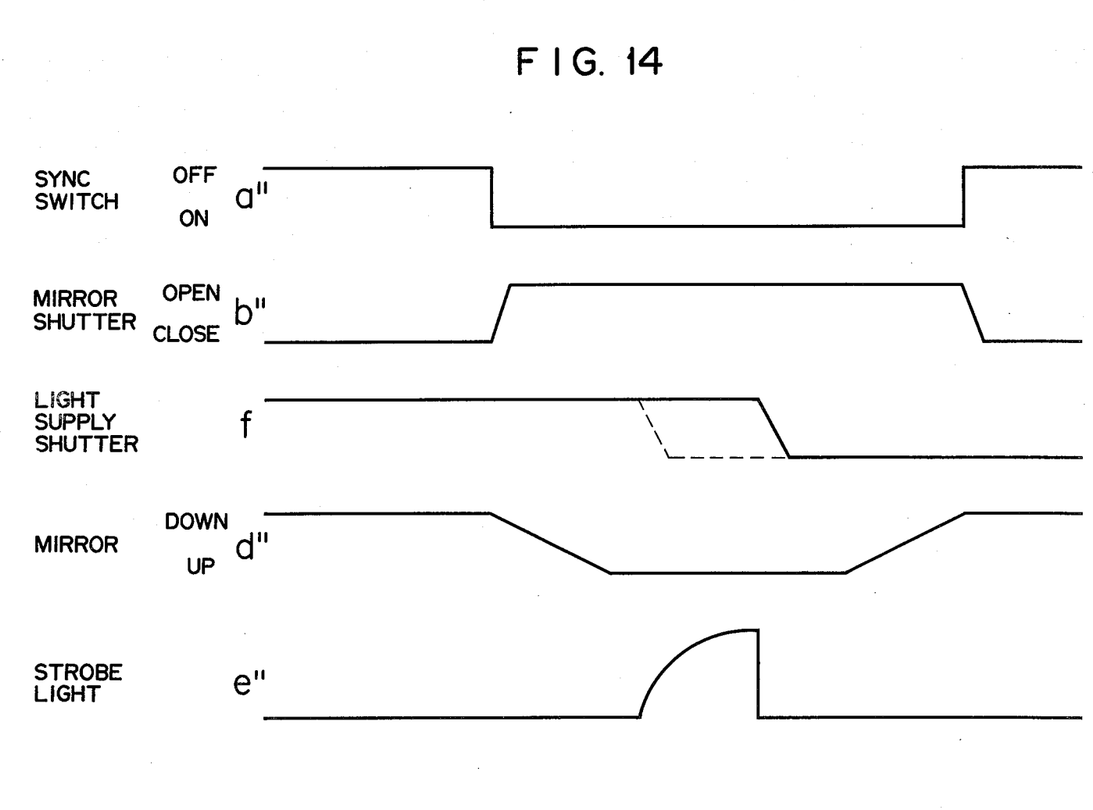

The operation of the endoscopic photographing apparatus wherein the conventional endoscopic camera 14 is combined with a newly-developed model i.e. new type of light supply unit 15 will be described referring to the time chart shown in FIG. 14. Since the conventional endoscopic camera 13 generates no response signal in response to the flag signal transmitted from the light supply unit 15, the CPU 62 of light supply unit 15 having no response applied discriminates that the endoscopic camera 13 is of conventional model or type. When the CPU 62 receives the sync signal from the conventional endoscopic camera 13, therefore, the strobo tube 63 is flashed without being delayed, as shown by the flow chart in FIG. 9. Namely, according to the time chart shown in FIG. 14, the mirror shutter is opened as shown by (b''), synchronizing with the closing of sync switch shown by (a''), and the light path exchanging mirror 67 of light supply unit 15 starts its light path exchanging operation this time as shown by (d'') while EE calculation is started. When the light path exchanging mirror 67 finishes its light path exchange, the strobo tube 63 is flashed as shown by (e''). Same operation will be thereafter repeated.

In a case where the endoscopic camera 13 is of new type and the light supply unit 15 is of conventional type, the CPU 21 of endoscopic camera 13 of newly-developed model discriminates that the light supply unit 15 connected is of conventional type when the CPU 21 receives no flag signal from the light supply unit 15 within a certain time period beginning from when the new type of endoscopic camera 13 is connected to the light supply unit 15. The new type of endoscopic camera 13 determines the timing at which the mirror shutter is opened, depending upon whether the light supply unit 15 is of new type or of conventional type. Namely, if the light supply unit 15 is of new type, the opening of mirror shutter is delayed until the light path exchanging mirror of light supply unit finishes its light path exchanging operation and if of conventional type, the mirror shutter is opened synchronizing with release operation.

As described above, the present invention provides an endoscopic photographing apparatus wherein at least one of endoscopic camera and light supply unit can discriminate whether the other is of new type or of conventional type and wherein photographing operation can be achieved according to the type discrimination. Therefore, the present invention enables the endoscopic camera and light supply unit to be easily combined with each other upon use whether they are of new type or conventional type. In addition, displays are kept unoperative until the model discrimination is finished and the result of EE enable calculation is obtained, so that undesirable display is not effected at the initial use of apparatus. It may also be arranged in this case that no display is effected until a type discrimination signal or search signal is received and that under-display is effected during the time period starting from the reception of search signal and ending with the reception of EE enable control signal. Although power is supplied from the light supply unit to the endoscopic camera, the power supply source may be arranged in the endoscopic camera or power source adaptor may be employed. Other photographing apparatus may be employed as well as the endoscopic camera.

What we claim is:

1. An endoscopic photographing apparatus comprising:

an endoscope having an eyepiece section and connector;

an endoscopic camera unit attached to the eyepiece section of said endoscope;

a light supply unit connected to the connector of said endoscope and emitting light to be guided into the endoscope;

a control section having means arranged in at least one of said endoscopic camera unit and said light supply unit for discriminating the type of endoscopic camera unit or light supply unit, depending upon the presence and absence of a response signal, when one of said endoscopic camera unit and light supply unit receives the response signal, said endoscopic camera unit and light supply unit executing a first photographing mode, and when one of said endoscopic camera unit and light supply unit receives no response signal, said unit having the control section executing a second photographing mode corresponding to an operation sequency of the other unit being without control section.

2. An endoscopic photographing apparatus according to claim 1 wherein said light supply unit is provided with discrimination means for generating a flag signal and for discriminating the type of the endoscopic camera depending upon the presence and absence of response in response to the flag signal.

3. An endoscopic photographing apparatus according to claim 2 wherein said endoscopic camera includes discrimination means for discriminating, in response to the flag signal, the type of said light supply unit and applying a response signal to said light supply unit.

4. An endoscopic photographing apparatus according to claim 1 wherein said endoscopic camera has the control section, which is connected to auto-exposure control means, and said auto-exposure control means carries out EE calculation in response to a sync signal applied from said control section so as to output an EE signal under optimum exposure.

5. An endoscopic photographing apparatus according to claim 1 wherein said endoscopic camera has display means for displaying various data and said control section is connected through a decoder to said display means.

6. An endoscopic photographing apparatus according to claim 5 wherein said decoder is a 3-to-8 decoder having an NC terminal floated.

7. An endoscopic photographing apparatus according to claim 1 wherein said light supply unit includes a lamp for emitting observation light, a lamp turn-on circuit for turning on said lamp, a strobo tube for emitting photographing flash light, a flash control circuit for controlling the light emission of said strobo tube, means for effecting the changeover of observation and flash lights, and a light shutter for shutting observation and flash lights, and said flash control circuit, turn-on circuit, light changeover means and shutter are driven by said control section.

* * * * *